United States Patent [19]

Hirai et al.

[11] Patent Number: 4,665,176

[45] Date of Patent: May 12, 1987

[54] PROCESS FOR THE PREPARATION OF 5,6,7,8-TETRAHYDROFOLIC ACID

[75] Inventors: Yutaka Hirai; Masaaki Torisu; Eri Nagayoshi, all of Fukuoka, Japan

[73] Assignee: Mitsui Toatsu Chemicals, Incorporated, Tokyo, Japan

[21] Appl. No.: 786,126

[22] Filed: Oct. 10, 1985

[30] Foreign Application Priority Data

Oct. 23, 1984 [JP] Japan .................................. 59-221189
Jun. 11, 1985 [JP] Japan .................................. 60-125130

[51] Int. Cl.$^4$ ............................................ C07D 475/04
[52] U.S. Cl. ...................................................... 544/258
[58] Field of Search ........................................ 544/258

[56] References Cited

U.S. PATENT DOCUMENTS 3,870,719  3/1975  Knott .................................. 544/258
4,540,783  9/1985  Viscontini ........................... 544/258
4,595,752  6/1986  Azuma ................................ 544/258

OTHER PUBLICATIONS

O'Dell, J. Amer. Chem. Soc., 69, pp. 250–253, (1947).

*Primary Examiner*—Sam Rosen
*Assistant Examiner*—Robert Benson
*Attorney, Agent, or Firm*—Fisher, Christen & Sabol

[57] ABSTRACT

A process for the preparation of 5,6,7,8-tetrahydrofolic acid which comprises dissolving and/or suspending folic acid or dihydrofolic acid in an aqueous solution containing an inorganic base, and bringing the resulting solution or suspension into contact with hydrogen in the presence of a noble metal catalyst while maintaining its pH at 5–9, thereby catalytically hydrogenating the folic acid of dihydrofolic acid into 4,5,6,7-tetrahydrofolic acid.

9 Claims, No Drawings

PROCESS FOR THE PREPARATION OF 5,6,7,8-TETRAHYDROFOLIC ACID

BACKGROUND OF THE INVENTION a. Field of the Invention

This invention relates to an improved process for the preparation of 5,6,7,8-tetrahydrofolic acid (hereinafter referred to briefly as tetrahydrofolic acid).

b. Description of the Prior Art

Tetrahydrofolic acid is a coenzyme represented by the structural formula (I) given below. This is a beneficial compound playing an important role in biosynthetic reactions. In enzymic reactions, for example, the $N^5,N^{10}$-formyl derivatives in which tetrahydrofolic acid is combined with formic acid serve as formyl donors, the $N^5,N^{10}$-methylene derivative in which tetrahydrofolic acid is combined with formaldehyde serves as a hydroxymethyl donor for converting glycine to serine, and the $N^5$-methyl derivative which is the reduced form of the methylene derivative serves to convert homocysteine to methionine.

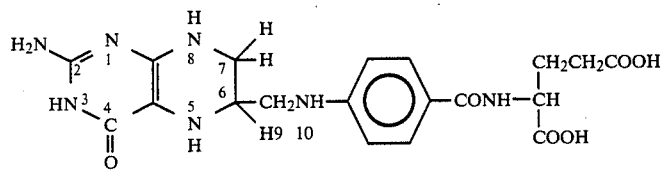

(I)

Conventionally, a number of processes for the preparation of tetrahydrofolic acid are known. One of them comprises dissolving folic acid in an aqueous solution of sodium hydroxide, reducing it with sodium hydrosulfite to form dihydrofolic acid, and further reducing it with sodium borohydride or the like to form tetrahydrofolic acid [Helv. Chim. Acta, 1980, 63(8), 2554] and another comprises reducing folic acid in acetic acid by means of NaCNBH₃ [Anal. Biochem., 1980, 103(2), 255]. However, these processes are not suitable for the purpose of producing tetrahydrofolic acid on an industrial scale because they have the disadvantages of requiring an expensive reducing agent in large amounts and involving troublesome procedures.

On the other hand, processes for the preparation of tetrahydrofolic acid by hydrogenating folic acid in the presence of a noble metal catalyst are also known. For example, U.S. Pat. Nos. 2,717,250 (1955) and 2,790,802 (1957) disclose a process comprising suspending folic acid in glacial acetic acid and reducing it in the presence of a platinum oxide catalyst. In this process, however, the amount of catalyst used is as much as 10 to 100% by weight based on the folic acid and a large amount of glacial acetic acid is used as the reaction solvent. Moreover, it requires a troublesome procedure for isolating the product. Furthermore, the yield of the product is as low as about 48%. Accordingly, this process cannot be regarded as economically beneficial.

In addition, an instance is found in which folic acid was dissolved in a large amount, i.e. about 19 moles per mole of the folic acid, of an aqueous sodium hydroxide solution (specifically, 36 mg of folic acid was dissolved in 15 cc of 0.1 N NaOH) and its hydrogenation was carried out under such strongly alkaline conditions in the presence of a platinum oxide catalyst used in an amount of as much as 70% by weight based on the folic acid [J. Am. Chem. Soc., 69, 250 (1947)]. In this instance, however, the hydrogenation stopped at the stage of dihydrofolic acid in spite of the large amount of catalyst used, so that only dihydrofolic acid was obtained in low yield and no tetrahydrofolic acid was produced.

Tetrahydrofolic acid is an unstable compound. With the lapse of time, tetrahydrofolic acid is decomposed by the action of oxygen, heat, light and the like to form dihydrofolic acid, folic acid, p-aminobenzoic acid and other compounds. Thus, where tetrahydrofolic acid has undergone a marked degree of deterioration, it sometimes inhibits enzymic reactions. Accordingly, the procedure for isolating tetrahydrofolic acid from the reaction solution obtained by catalytic hydrogenation of folic acid is carried out in an atmosphere of an inert gas (for example, in a box purged with nitrogen gas to replace the air present therein) in order to prevent the tetrahydrofolic acid from being deteriorated by oxidation.

Where the tetrahydrofolic acid thus obtained is in powder form, it is sealed in ampules filled with an inert gas such as argon gas and the like. Where it is in the form of a solution, it is dissolved in an aqueous solution containing 1 mole/liter of mercaptoethanol so as to give a typical concentration of the order of 0.5 g/3 ml, and sealed in ampules filled with an inert gas in the same manner as for powder products. These ampules are solid in a refrigerated state.

As described above, the conventionally known processes for the preparation of tetrahydrofolic acid have not been satisfactory for the purpose of producing it on an industrial scale because hydrogenolysis and the like may cause the formation of by-products during hydrogenation and the reaction mixture may contain residual unreacted folic acid or dihydro compound, resulting in a low yield of the desired product.

Moreover, the conventional methods for stabilizing and storing tetrahydrofolic acid have been effective to a certain degree, but not entirely satisfactory. Specifically, even if a stabilizer such as mercaptoethanol or the like is contained, the stability of a tetrahydrofolic acid solution depends largely on temperature. That is, it undergoes deterioration even at relatively low temperatures around 0° C. and especially remarkable deterioration in quality at room temperature and its vicinities, indicating that the stabilizer does not function properly. Though the storage stability of a powder is better than that of a solution, its deterioration in quality with time has also been unavoidable because it is difficult to substitute an inert gas for the air present in the container in cases where the unused portion of the tetrahydrofolic acid taken out of an ampule is stored again or tetrahydrofolic acid prepared by the user is stored in a container for purposes of captive consumption. Accordingly, it would be desirable to improve the storage stability of tetrahydrofolic acid.

SUMMARY OF THE INVENTION

It is an object of the present invention to provide a process for preparing tetrahydrofolic acid in high yield.

It is another object of the present invention to provide an economically beneficial and simplified process for preparing tetrahydrofolic acid.

It is a further object of the present invention to provide a method for manufacturing tetrahydrofolic acid products having storage stability.

According to the present invention, these objects can be accomplished by a process for the preparation of tetrahydrofolic acid which comprises dissolving or suspending folic acid or dihydrofolic acid in an aqueous solution containing an inorganic base, and catalytically hydrogenating the folic acid or dihydrofolic acid to tetrahydrofolic acid in the presence of a noble metal catalyst such as platinum or rhodium while maintaining the pH of the reaction mixture in the range of 5 to 9.

Tetrahydrofolic acid may be used in the form of the reaction solution obtained by separating the catalyst from the reaction mixture or in the form of a powder isolated from the reaction mixture. In such cases, it is desired to provide a simple method for storing tetrahydrofolic acid stably for a long period of time. This desire can be satisfied by freezing an aqueous solution containing tetrahydrofolic acid and an inorganic base, and sealing the frozen solution in an atmosphere of an inert gas so as to shield it from air; or by sealing a powder of tetrahydrofolic acid, together with a deoxidizer, in an atmosphere of an inert gas so as to shield it from air. According to either of these methods, tetrahydrofolic acid can be stored stably.

DETAILED DESCRIPTION OF THE INVENTION

In the process of the present invention, folic acid or dihydrofolic acid is used as the starting material.

The inorganic base used in the process of the present invention can be any inorganic base that allows folic acid or dihydrofolic acid to dissolve and exerts no adverse influence on the hydrogenation reaction. Specific examples of such inorganic bases include sodium hydroxide, potassium hydroxide, sodium carbonate, potassium carbonate, sodium hydrogen carbonate, potassium hydrogen carbonate, ammonium hydroxide and the like. Among others, ammonium hydroxide is preferred.

The amount of inorganic base used should usually be in the range of 0.5 to 1.5 equivalents for each equivalent of the carboxyl groups of the starting folic acid or dihydrofolic acid and may be suitably determined according to the type of inorganic base used and the pH of the reaction mixture. However, the amount of inorganic base used should preferably be an approximately equivalent amount, i.e., in the range of 0.8 to 1 equivalent for each equivalent of the carboxyl groups of the starting folic acid or dihydrofolic acid. The reaction should be carried out in such a way that the pH of the reaction mixture is maintained in the range of 5 to 9 and preferably in the range of 6 to 8.

If the pH of the reaction mixture is less than 5, the solubility of the starting material is reduced and, therefore, a large amount of unreacted material will remain. If the pH of the reaction mixture is greater than 9, the activity of the catalyst is reduced. Thus, the amount of hydrogen absorbed will become much less than the theoretical value, so that the reaction will stop halfway and a large amount of unreacted material will remain.

At the initial stage of the reaction, the folic acid used as the starting material need not be completely dissolved, but may be present in such a state that at least about a half of it is dissolved and the remainder is suspended. In such a case, the inorganic base should be added cumulatively with the progress of the reaction. Thus, the product is finally obtained in the form of an aqueous solution.

In carrying out the process of the present invention, all the approximately equivalent amount of inorganic base may be charged into the reaction system at the beginning of the reaction. However, it is more preferable to charge a part of the inorganic base into the reaction system at the beginning of the reaction and add the remainder drop by drop as the hydrogenation reaction proceeds. This technique makes it possible not only to moderate the reaction properly and maintain the activity of the catalyst, but also to minimize the formation of by-products by hydrogenolysis of tetrahydrofolic acid.

A noble metal catalyst is used in the process of the present invention, and preferred examples thereof are platinum and rhodium. Usually, such catalysts are used by supporting them on activated carbon, silica, alumina and the like. They can also be used in the form of oxides such as platinum oxide.

When expressed in terms of the noble metal, the amount of catalyst used should be in the range of 0.15 to 3.0% by weight based on the folic acid used as the starting material or in the range of 0.15 to 2.0% by weight based on the dihydrofolic acid used as the starting material. For example, where a 5% platinum-activated carbon catalyst is used, it is usually suitable to use the catalyst in an amount of 3 to 20% based on the folic acid. Where folic acid is used as the starting material, if the amount of 5% platinum-activated carbon catalyst used is less than 3%, the reaction will stop halfway and leave unreacted material and intermediate products. If the amount of catalyst used is greater than 20% by weight, the reaction will be completed in a short period of time, but there will be an undesirable tendency to cause the formation of by-products by hydrogenolysis. Generally, a fresh catalyst need not be used in so large amounts. The preferred range is usually from 5 to 15% by weight. The catalyst which has been used in the reaction is separated by filtration or other means, washed with water and reused in subsequent reactions. Since the activity of the catalyst is more or less reduced, a fresh catalyst should be added according to the need.

The pressure of hydrogen used in the hydrogenation may be atmospheric pressure. However, the reaction can be carried out at superatmospheric pressures, if necessary.

The reaction temperature at which the hydrogenation is carried out may suitably be 0° C. or above. Where the reaction is carried out at atmospheric pressure, it is desirable to use a temperature in the range of 0° to 80° C. The especially preferred range is from 20° to 50° C.

Since the rate of the hydrogenation reaction depends largely on the rate of stirring of the reaction mixture, it is preferable to stir the reaction mixture vigorously so as to bring it into intimate contact with hydrogen.

The procedure for isolating tetrahydrofolic acid from the reaction mixture is usually carried out in an atmosphere of an inert gas so as to prevent the tetrahydrofolic acid from being deteriorated by oxidation. Specifically, in a box purged with nitrogen to replace the air present therein, the catalyst is separated from the reaction mixture by filtration or other means. Then, in the presence of a stabilizer such as L-ascorbic acid, mercaptoethanol or the like, the resulting solution is neutralized with hydrochloric acid to precipitate the tetrahydrofolic acid. It is preferable to neutralize the solution until its pH comes in the vicinity of 3.5.

After cooling, the neutralized solution is subjected to a separation procedure such as filtration or the like. The tetrahydrofolic acid separated by filtration is washed with deaerated cold water to remove any salts, and then dried.

In order to dry the tetrahydrofolic acid at low temperatures in a short period of time, it is preferable to wash it with a low-boiling and water-miscible solvent (such as acetone, methanol or the like) prior to drying.

The tetrahydrofolic acid thus obtained is in the form of white to ash-gray crystals and usually has a purity of not less than 80% (as determined by HLC analysis). Without any further purification, it exhibits an activity sufficient for use as a coenzyme in enzymic reactions.

Moreover, a tetrahydrofolic acid product having long-term storage stability can be obtained by preparing tetrahydrofolic acid in the form of a solution, sealing it in a container filled with an inert gas and storing it in a frozen state. The solution can be the reaction solution obtained by separating the catalyst from the reaction mixture having subjected to the above-described hydrogenation, or an aqueous solution obtained by isolating the tetrahydrofolic acid in powder form as described above and dissolving the powder in an aqueous solution of an alkali (such as ammonium hydroxide, sodium hydroxide or the like) so as to give a typical concentration of 5 to 10% by weight. It has been found that no adverse influence is noted when the frozen solution is thawed and used, for example, in an enzymic reaction for the synthesis of L-serine.

Where the tetrahydrofolic acid is stored in powder form, this may usually be accomplished by sealing the powder, together with a deoxidizer, in a container filled with an inert gas and storing it at low temperatures. The deoxidizer can be any well-known oxygen absorbing substance packed in a porous material, for example, the one commercially available from Mitsubishi Gas Chemistry Co., Ltd. under the trade name of AGELESS. The amount of deoxidizer used may be suitably determined according to the amount of tetrahydrofolic acid stored and the period of storage. Where such a deoxidizer is present in a sealed container, the interior of the container will be reduced in pressure as a result of deoxidization. Accordingly, in sealing the powder together with the doxidizer, the container should preferably be filled with an inert gas so as to establish a slightly pressurized state therein. The sealed container should be stored at low temperatures lower than 0° C.

According to the process of the present invention, the production cost is very low because an aqueous solution of a cheap inorganic base is used as the solvent, and the reaction is completed in a relatively short period of time because the starting material can be hydrogenated in such a state that it is totally dissolved in the aqueous solution of the inorganic base or mostly dissolved therein with the remainder suspended therein. Accordingly, a very small amount of catalyst is sufficient for the purpose of the present invention. Moreover, the after-treatment of the reaction mixture is also simplified. Specifically, this may be accomplished by filtering the reaction mixture to separate the catalyst therefrom, pouring the filtrate into an acid solution containing a stabilizer such as L-ascorbic acid or the like, and thereby neutralizing the filtrate to precipitate the desired product. The precipitate so formed may be separated by filtration, washed and then dried under reduced pressure. Thus, a high-quality preparation of tetrahydrofolic acid which can be satisfactorily used in such reactions as the biosynthesis of L-serine and the like is obtained in good yield without requiring any further purification.

Furthermore, tetrahydrofolic acid products having good long-term storage stability can be obtained by preparing the reaction product in the form of a solution (i.e., the reaction solution obtained by separating the catalyst from the aforesaid reaction mixture having subjected to hydrogenation, or an aqueous solution formed by isolating the reaction product in powder form and dissolving it in an aqueous solution of an alkali such as ammonium hydroxide, sodium hydroxide or the like), freezing and solidifying the solution, and shielding it from air; or by isolating the reaction product in powder form and sealing the powder, together with a deoxidizer, in an inert gas to shield it from air.

The process of the present invention is more specifically illustrated by the following examples. The folic acid used in these examples had a purity of 91.3% and its number of moles is expressed in terms of pure folic acid.

EXAMPLE 1

Into a 1-liter round bottom flask fitted with a baffle were charged 15.012 g ($3.105 \times 10^{-2}$ moles) of folic acid and 10.8 ml ($5.40 \times 10^{-2}$ moles) of a $\frac{1}{2}$-N aqueous solution of ammonium hydroxide. The contents were stirred until the greater part of the folic acid dissolved. The resulting solution exhibited a pH of 6.6.

Then, a suspension of 2.025 g of a 3% platinum-activated carbon catalyst (containing the noble metal in an amount of 0.44% by weight based on the folic acid) in 160 ml of distilled water was added to the flask. After the interior of the system was purged with nitrogen, hydrogenation was carried out at atmospheric pressure for 360 minutes with the contents of the flask stirred vigorously in the usual manner. At the end of the reaction, the amount of hydrogen absorbed was 100.4% of the theoretical value.

After completion of the reaction, 18.6 ml of a $\frac{1}{2}$-N aqueous solution of ammonium hydroxide was added under a stream of nitrogen gas to dissolve the insoluble matter which was present in very small amounts. From this step forward, the separation and drying of the reaction product was always carried out in an atmosphere of nitrogen.

Specifically, the reaction mixture was filtered with a suction filter to separate the catalyst, which was washed with 30 ml of distilled water. Then, the filtrate and the washings were poured into a solution of 3.3 g of L-ascorbic acid in 117.4 ml of $\frac{1}{2}$-N hydrochloric acid. The resulting mixture was neutralized to adjust its pH to 3.5. The precipitate so formed was separated by suction filtration and washed with 30 ml of distilled water at 5° C. and then with 200 ml of acetone at 5° C. The resulting wet cake was placed in a dryer containing a desiccating agent and kept at a reduced pressure of 5 mmHg, and dried at 25°–30° C. for 8 hours to obtain 10.714 g (77.5% yield) of tetrahydrofolic acid.

The tetrahydrofolic acid thus obtained had a purity of 85.0% as analyzed by high-speed liquid chromatography. When this product was used in enzymic reactions without further purification by conventional techniques such as column chromatography and the like, it exhibited an activity equivalent to those of commercially available reagent grade products.

EXAMPLE 2

Into a 300-ml round bottom flask fitted with a baffle were charged 4.310 g ($8.91 \times 10^{-3}$ moles) of folic acid and 32.2 ml ($16.1 \times 10^{-3}$ moles) of a $\frac{1}{2}$-N aqueous solution of ammonium hydroxide. The contents were stirred until the greater part of the folic acid dissolved. The resulting solution exhibited a pH of 6.6.

Then, a suspension of 0.0687 g of platinum oxide (containing the noble metal in an amount of 1.5% by weight based on the folic acid) in 50 ml of distilled water was added to the flask, and hydrogenation was carried out in the same manner as described in Example 1 to obtain 2.973 g (74.9% yield) of tetrahydrofolic acid.

EXAMPLE 3

Into a 300-ml round bottom flask fitted with a baffle were charged 2.2963 g ($4.75 \times 10^{-3}$ moles) of folic acid and 16.5 ml ($8.25 \times 10^{-3}$ moles) of a $\frac{1}{2}$-N aqueous solution of ammonium hydroxide. The contents were stirred until the greater part of the folic acid dissolved. The resulting solution exhibited a pH of 6.5.

Then, a suspension of 0.230 g of a 5% rhodium-activated carbon catalyst (containing the noble metal in an amount of 0.55% by weight based on the folic acid) in 25 ml of distilled water was added to the flask, and hydrogenation was carried out in the same manner as described in Example 1 to obtain 1.593 g (75.3% yield) of tetrahydrofolic acid.

EXAMPLE 4

Into a 300-ml round bottom flask fitted with a baffle were charged 4.384 g ($9.07 \times 10^{-3}$ moles) of folic acid and 35.7 ml ($17.85 \times 10^{-3}$ moles) of a $\frac{1}{2}$-N aqueous solution of ammonium hydroxide. The contents were stirred until the greater part of the folic acid dissolved. The resulting solution exhibited a pH of 7.3.

Then, a suspension of 0.399 g of a 5% platinum-activated carbon catalyst in 50 ml of distilled water was added to the flask, and hydrogenation was carried out for 515 minutes in the same manner as described in Example 1. At the end of the reaction, the amount of hydrogen absorbed was 101.8% of the theoretical value.

After the catalyst was separated by filtration, the filtrate was poured into a solution consisting of 34 ml of $\frac{1}{2}$-N hydrochloric acid and 1.026 g of L-ascorbic acid. The resulting mixture was neutralized to adjust its pH to 3.5.

The reaction product was separated and dried in the same manner as described in Example 1 to obtain 2.926 g (72.4% yield) of tetrahydrofolic acid.

EXAMPLE 5

Into a 300-ml round bottom flask fitted with a baffle were charged 2.179 g of 7,8-dihydrofolic acid and 17.5 ml of a $\frac{1}{2}$-N aqueous solution of ammonium hydroxide. The contents were stirred until the greater part of the dihydrofolic acid dissolved. The resulting solution exhibited a pH of 6.7.

Then, 0.112 g of a 5% platinum-activated carbon catalyst (containing the noble metal in an amount of 0.26% by weight based on the dihydrofolic acid) was added to the flask, and hydrogenation was carried out in the same manner as described in Example 1 to obtain 1.439 g (65.7% yield) of tetrahydrofolic acid.

EXAMPLE 6

10.0 ml (0.5 equivalent) of $\frac{1}{2}$-N ammonium hydroxide was added to 2.417 g ($5.0 \times 10^{-3}$ moles) of folic acid and the resulting solution was adjusted to pH 6.3. Then, 0.202 g of a 5% platinum-activated carbon catalyst and 25 ml of distilled water were added to initiate the hydrogenation.

From the time when the hydrogen absorption rate began to descrease, 9.8 ml of a $\frac{1}{2}$-N aqueous solution of ammonium hydroxide was slowly added little by little to the reaction mixture with the progress of the reaction. Finally, the reaction mixture exhibited a pH of 6.8.

Thereafter, the reaction mixture was worked up in the same manner as described in Example 1 to obtain 1.785 g (80.2% yield) of tetrahydrofolic acid.

EXAMPLE 7

10.0 g of a powder of tetrahydrofolic acid (88.8% pure) containing 1.0% of L-ascorbic acid as a stabilizer, together with a deoxidizer pack (commercially available from Mitsubishi Gas Chemistry Co., Ltd. under the trade name of AGELESS) having an oxygen absorption capacity of 50 cc, was charged into a 100-cc brown sample tube made of glass. This tube was purged with $N_2$ gas to replace the air present therein, and then sealed tightly. (This sample will hereinafter be referred to as Sample A.)

On the other hand, a control sample was sealed in a sample tube under the same conditions except that no deoxidizer was placed therein (Sample B). Both samples were stored in a thermostatic chamber kept at $-20°$ C. and their changes in purity with time were examined by high-speed liquid chromatography. The results thus obtained are shown in Table 1, clearly indicating the effect of the deoxidizer.

TABLE 1

| Changes of Tetrahydrofolic Acid (Powder) with Time | | | | |
|---|---|---|---|---|
| | Number of days | | | |
| Sample | 0 | 10 | 20 | 40 |
| A (with deoxidizer) | 88.8 | 88.3 | 88.3 | 88.0 |
| B (control sample) | 88.8 | 80.0 | 74.5 | 70.6 |

EXAMPLE 8

100 g of folic acid (91.3% pure) was dissolved in an equivalent amount of dilute aqueous ammonia to form a solution having a concentration of 10.0% by weight, to which 8.14 g of a 3% platinum-activated carbon catalyst (with a water content of 50%) was added. After the system was purged with nitrogen and then with hydrogen, hydrogenation was carried out in the neutral region at room temperature and atmospheric pressure according to conventional procedure.

After completion of the reaction, the system was purged with nitrogen to replace the hydrogen present therein and then placed in a nitrogen box, where 21.4 g of L-ascorbic acid was added to the reaction mixture and dissolved therein by stirring. Then, the catalyst was separated by suction filtration and washed with 100 cc of deaerated water to obtain an aqueous solution of tetrahydrofolic acid ammonium salt.

150 cc each of the above aqueous solution of tetrahydrofolic acid ammonium salt containing 1.74% of L- ascorbic acid (and having a tetrahydrofolic acid concentration of 7.13%) was charged into 250-cc brown tubes made of glass. These tube was purged with nitrogen gas to replace the air present therein, and then sealed tightly.

These tubes were stored in thermostatic chambers kept at −20° C., 0°–5° C. and 25° C., respectively, and their changes in tetrahydrofolic acid concentration with time were examined by high-speed liquid chromatography. The results thus obtained are shown in Table 2, clearly indicating that the quality of an aqueous tetrahydrofolic acid solution is stabilized by freezing and storing it at low temperatures.

TABLE 2

Changes with Time in Tetrahydrofolic Acid Concentration of a Solution

| Storage temperature (°C.) | Number of days | | | |
|---|---|---|---|---|
| | 0 | 20 | 40 | 60 |
| −20 (frozen) | 7.13 | 7.04 | 6.97 | 6.93 |
| 0–5 | 7.13 | 4.77 | 3.91 | 2.50 |
| 25 | 7.13 | 1.95 | 1.55 | 1.07 |

What is claimed is:

1. Process for the preparation of 5,6,7,8-tetrahydrofolic acid, consisting of dissolving or suspending folic acid or dihydrofolic acid in an aqueous solution containing an inorganic base, the inorganic base being selected from the group consisting of ammonium hydroxide, sodium hydroxide, potassium hydroxide, sodium carbonate, potassium carbonate, sodium hydrogen carbonate and potassium hydrogen carbonate, and bringing the resultant folic acid-containing or dihydrofolic acid-containing solution or suspension into contact with hydrogen in the presence of a catalytic amount of noble metal while maintaining its pH in the range of 5 to 9, the noble metal being selected from the group consisting of platinum supported on a carrier, rhodium supported on a carrier and platinum oxide supported on a carrier, the noble metal being used in an amount of 0.15 to 3.0 percent by weight based on the weight of the folic acid, or dihydrofolic acid, whereby the folic acid or dihydrofolic acid is catalytically hydrogenated to 5,6,7,8-tetrahydrofolic acid.

2. The process as claimed in claim 1 wherein the pH range of 5 to 9 is maintained by cumulatively adding the inorganic base.

3. The process as claimed in claim 1 wherein the inorganic base is an aqueous solution of ammonium hydroxide.

4. The process as claimed in claim 1 wherein the inorganic base is used in an amount of 0.8 to 1 equivalent for each equivalent of the carboxyl groups of the folic acid or dehydrofolic acid.

5. The process as claimed in claim 1 wherein the noble metal is used in an amount of 0.15 to 2.0 percent by weight based on the weight of the folic acid or dihydrofolic acid.

6. The process as claimed in claim 1 wherein the catalytic hydrogenation is carried out at a temperature of 0° to 80° C.

7. The process as claimed in claim 1 wherein the catalytic hydrogenation is carried out at atmospheric pressure.

8. Method for the manufacture of a 5,6,7,8-tetrahydrofolic acid product capable of being stably stored at low temperatures which consists of filtering the reaction mixture obtained by the process as claimed in claim 1 to separate the noble metal therefrom, freezing and solidifying the resultant aqueous solution containing 5,6,7,8-tetrahydrofolic acid and the inorganic base, and sealing the frozen solution in an atmosphere of an inert gas.

9. The method for the manufacture of a 5,6,7,8-tetrahydrofolic acid product capable of being stably stored at low temperatures which consists of isolating a powder of 5,6,7,8-tetrahydrofolic acid from the reaction mixture obtained by the process as claimed in claim 1, and sealing the powder, together with a deoxidizer, in an atmosphere of an inert gas.

* * * * *